United States Patent [19]

Knowlton

[11] 4,417,476

[45] Nov. 29, 1983

[54] CHARGE CONVERTER FOR VIBRATION MONITORING INSTRUMENTATION

[75] Inventor: William K. Knowlton, Rexford, N.Y.

[73] Assignee: General Electric Company, Schenectady, N.Y.

[21] Appl. No.: 364,468

[22] Filed: Apr. 1, 1982

[51] Int. Cl.³ .............................................. G01H 1/00
[52] U.S. Cl. ..................................................... 73/660
[58] Field of Search ................. 73/658, 659, 660, 661, 73/649; 310/319, 329, 334, 336; 340/683, 682

[56] References Cited

U.S. PATENT DOCUMENTS 3,455,148  7/1969  Foster et al. .......................... 73/660

OTHER PUBLICATIONS

Instruction Manual, Model 2735 Charge Amplifier, Endevco, Pasadena, Calif. (Apr. 1978) pp. 3-9 to 3-12, 5-1 to 5-3, 6-1, and circuit diagram.
Handbook of Operational Amplifier Circuit Design, Stout & Kaufman, McGraw-Hill (1976) p. 4-19.

*Primary Examiner*—Stephen A. Kreitman
*Attorney, Agent, or Firm*—Robert C. Kain, Jr.; John F. Ahern

[57] ABSTRACT

Apparatus for monitoring mechanical vibrations in a component part of an operating machine such as a large electrical power generator includes an electric charge producing transducer, preferably a piezoelectric accelerometer, affixed to the component part of the machine to be monitored, and a charge converter network located within the machine but relatively remote from the transducer. The charge converter network accepts the signal from the transducer, in the form of electrical charge generated at a rate and magnitude representative of the mechanical vibrations, and converts the charge signal to a conventional electronic signal. The charge converter network includes a differential operational amplifier having a resistive-capacitive feedback network providing equal impedance values to a corresponding resistive-capacitive network at the noninverting input of the amplifier. The transducer output is applied between the differential input terminals of the amplifier. The output signal is substantially free of the effects of common mode signals and other electrical interferences arising from a severe electrical environment such as that found within an electrical power generator.

7 Claims, 1 Drawing Figure

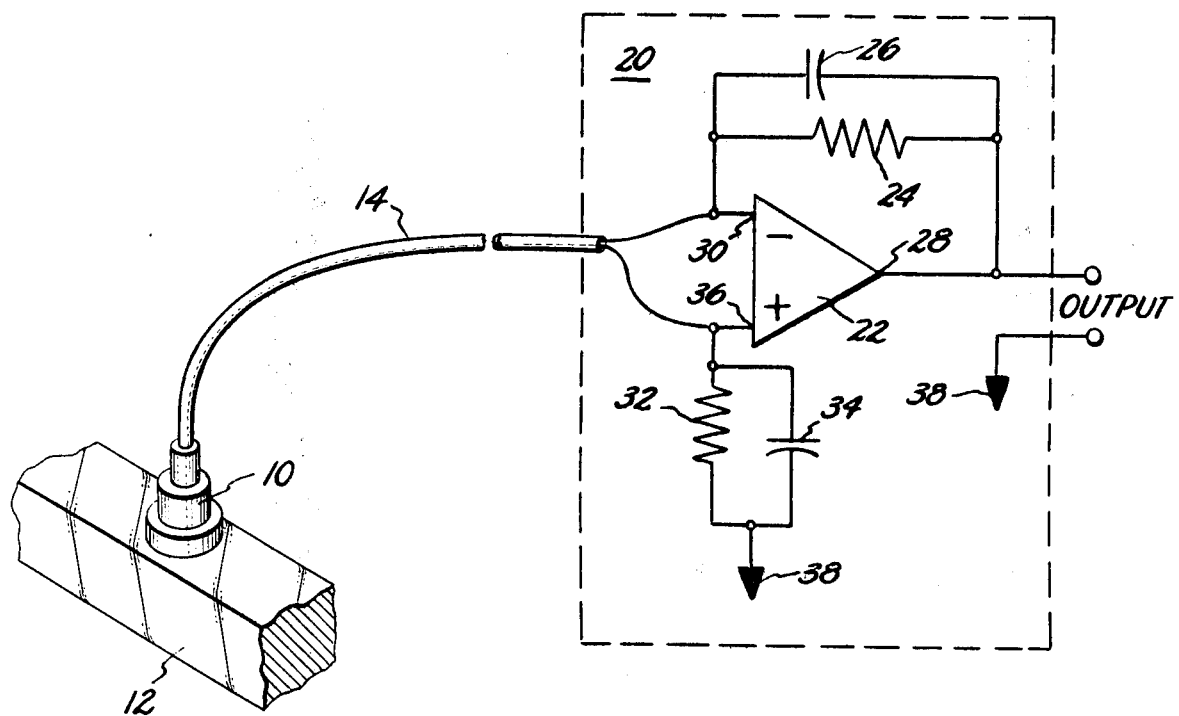

CHARGE CONVERTER FOR VIBRATION MONITORING INSTRUMENTATION

BACKGROUND OF THE INVENTION

The present invention pertains generally to instrumentation for monitoring physical parameters of operating machines and more particularly to instrumentation for monitoring mechanical vibrations of component parts of large electrical power generators.

It is frequently desirable or necessary to determine the magnitude and/or pattern of mechanical vibrations in some part of an operating machine. For example, in some machines it may be necessary to continuously monitor vibrations in order to initiate protective action in case there is a trend toward destructive levels of vibration. In other situations, vibration information might be sought in order to carry out a test program for machine development or in order to pinpoint the source or cause of vibrations.

One application for vibration monitoring is the large electrical power generators used by the utility companies for generating power on a commercial scale. In these machines, it is particularly desirable to determine the vibrations occurring in the connection rings which electrically interconnect the phase windings and which carry the load current to bushings leading through the generator casing. These connection rings carry thousands of amperes of current at voltage levels running well into the kilovolt range. Vibrations can arise in the connection rings as a result of the intense electromagnetic forces within the generator which in turn are caused by the large alternating current flows and by the rotating magnetic field. The connection rings are mechanically restrained to the extent possible, of course, and flexible joints are used to absorb vibrations so that they are not transmitted to the output bushings of the generator.

To protect the connection rings and flexible joints from fatigue failure due to vibrations, means have long been sought which would allow vibrations to be continuously monitored in these and other structural members of the generator. Obtaining accurate vibration information from these rings, however, and indeed from other components of these machines, has been hampered by the necessity of having a vibration sensor and its associated circuitry located within the close confines of the generator wherein they are exposed to the effects of high current voltage, and intense electromagnetic fields. The conventional vibration monitoring method in which a piezoelectric accelerometer transducer, attached to the vibrating component, generates electrical charge to be converted into a conventional electronic signal by a charge converter, has not been entirely successful due to the hostile electrical environment and to the relatively tight spacings around the generator end windings. The problems, however, generally have been associated more with the charge converter than with the transducer, and with the need for isolation between the electronic circuitry and the remote (external to the generator) signal handling circuitry.

Conventional charge converters are generally of two types. The first type is a simple circuit consisting of an operational amplifier having a negative feedback loop which includes a capacitor which is responsive to be charged by the electrical charge generated by the transducer. The transducer output is connected directly to the input terminals of the operational amplifier. While this type of charge converter is small, uncomplicated, and can be fitted well into the tight spacing around generator end windings, it suffers from an inability to provide good common mode rejection, ground loop isolation, and freedom from the effects of the differences in potential arising in interconnecting cabling and so forth as a result of the severe electrical environment within the generator. These latter drawbacks particularly hamper charge converters if they are to be used in generators wherein large common mode signals and other electrical interferences are readily generated by the current and voltage produced by the machine. Under such conditions, the vibration signal is simply overwhelmed and lost if the common mode signals and interferences are not rejected. Furthermore, significant errors arise from ground loops caused by significantly different potentials appearing at common connection points relatively close together physically.

The second type of conventional charge converter partially overcomes the common mode rejection and ground loop problems by using a number of discrete components, separate isolated power supplies, and isolation amplifiers. However, the circuitry is quite complex and is not readily adaptable to use in an electric generator.

Accordingly, it is among the objects of the present invention to provide apparatus for monitoring mechanical vibrations in a component part of an operating machine wherein the apparatus is simple, economical to manufacture and install, is particularly adaptable to installation in and around the end windings of a large electrical power generator, is operable to provide a high degree of immunity to undesired common mode signal components, and other electrical interferences and is substantially free of ground loop effects.

SUMMARY OF THE INVENTION

In a preferred form of the invention, apparatus for monitoring mechanical vibrations in a component part of an operating machine includes an electric charge producing transducer (preferably a piezoelectric accelerometer) affixed to the component part of the machine to be monitored, and a charge converter network located within the machine but not necessarily in juxtaposition to the transducer. The charge converter network accepts the output signal from the transducer, in the form of electrical charge generated at a rate and magnitude representative of the mechanical vibrations, and converts the charge signal to a conventional electronic signal, i.e., a voltage and current representation of the mechanical vibrations.

The charge converter network includes a differential operational amplifier, a first resistor-capacitor pair connected in parallel between the amplifier output terminal and its inverting input terminal, and a second resistor-capacitor pair connected from the non-inverting input terminal of the amplifier to the circuit common point. The transducer output is connected directly between the differential input terminals of the amplifier. Preferably, the resistance and capacitance values are of equal corresponding value providing equal impedance at all frequencies.

The invention is particularly useful in monitoring vibrations in components of an electrical generator, wherein it provides a high degree of immunity to common mode signals and other electrical interferences inherent in such use and wherein it is effective to eliminate or substantially minimize the effects of grounding loops. In tests of the invention, very suprising and unexpected superiority over conventional charge converted networks is demonstrated in freedom from interference effects.

DESCRIPTION OF THE PREFERRED EMBODIMENT

Referring now to the drawing, a vibration transducer 10, in the form of a piezoelectric accelerometer, is affixed to a component part 12 of the machine to be monitored. For example, component 12 may be one of the connection rings located in the end winding section of the stator winding of a large electrical generator. Such connection rings are typically covered over with a layer of insulating tape. In any case, it is preferable to secure transducer 10 to ring 12 by a suitable adhesive such as, for example, an epoxy adhesive. However, attachment of transducer 10 to ring 12 may be carried out by any appropriate means. It will be recognized, of course, that only a segment of the entire connection ring is illustrated and that other portions of the machine not material to an understanding of the invention have been omitted from the drawing for simplicity.

The accelerometer 10, being of the piezoelectric type, is a self-generating device requiring no electrical excitation. The electrical charge generated is proportional to acceleration and hence accelerometer 10 responds to mechanical vibrations in ring 12 to which it is attached. The output signal from the transducer 10, in the form of electrical charge, is conveyed via shielded cable 14 to a charge converter network 20 which is operative to convert the charge signal to a conventional electronic signal indicative of vibrations in ring 12. Charge converter 20 is located within the machine under test, although it may be necessary, particularly in an electrical generator, to locate the converter 20 relatively remote from the accelerometer 10, e.g., 10 feet or so away.

Charge converter 20 includes a differential operational amplifier 22, a feedback resistor 24 in parallel with a capacitor 26 connected between the output port 28 and the inverting input port 30 of the operational amplifier 22, and an input resistor 32 in parallel with a second capacitor 34 connected between the non-inverting input 36 of the operational amplifier 22 and a circuit common point 38. The shield wire of cable 14 is connected directly to the non-inverting input 36, and the central conductor of cable 14 is connected directly to the inverting input 30. An analog output signal characteristic of vibrations in ring 12 is taken from the output port 28 of the operational amplifier 22 and is referenced to the common point 38. The output signal may be transmitted by any suitable means to a point outside the machine where it can then be conditioned, if necessary, for recording and/or display.

It will be understood, however, that suitable isolation must be provided between the signal generation circuitry located within a large electrical generator and any external signal processing apparatus. Thus, the circuitry illustrated herein may, in its entirety, be expected to operate at a very high potential. Suitable isolation may be provided, for example, by conventional telemetry techniques, use of battery power supplies, and so forth. These techniques are providable by those of ordinary skill in the art. Preferably, operational amplifier 22 is a model LM 108 available commercially from the National Semiconductor Corporation while resistors 24 and 32 are of equal value at 200 megohms each, and capacitors 26 and 34 are each 220 picofarads. Accelerometer 10 may be a model 2222C manufactured and sold by Endevco of Pasadena, Calif.

Conventional charge converters, using a simple resistor and capacitor feedback path, provide an output voltage $V_0$ according to the formula:

$$V_o = \frac{q}{C}\left(\frac{R}{R + \frac{1}{\omega c}}\right) \cos \omega t$$

where q is the instantaneous charge generated by the transducer; R is the value of feedback resistance; C is the value of the feedback capacitor; $\omega$ is the angular frequency; and t is time. With the charge converter of the present invention, however, the output voltage is twice as great as that produced by the conventional charge converter. In particular, the output of the present invention is according to the formula:

$$V_o = \frac{2q}{C}\left(\frac{R}{R + \frac{1}{\omega c}}\right) \cos \omega t$$

Thus there is an inherently higher signal amplification in the charge converter of the present invention.

The charge converter of the present invention has been found to provide excellent rejection of common mode signals (i.e., rejection of those signals appearing simultaneously at both inputs of the operational amplifier 22) and freedom from the effects of differences in potential which appear at opposite ends of the conductors of cable 14 (particularly in the shield, or outer conductor). Furthermore, the effects of different electrical potentials appearing at different common connection points, commonly referred to as ground loops, have been substantially eliminated. Thus, the present invention provides a high degree of accuracy even when operated in a most hostile electrical environment such as that encountered when obtaining vibration information from an electrical power generator.

While there has been shown and described what is considered a preferred embodiment of the invention, it is understood that various other modifications may be made therein. It is intended to claim all such modifications which fall within the true spirit and scope of the present invention.

What is claimed is:

1. Apparatus for monitoring mechanical vibrations in a component part of an operating machine under conditions producing severe electrical interference, comprising:
    a transducer affixed to said component part and responsive to said vibrations to generate a first signal, in the form of electrical charge, characteristic of said vibrations;
    a charge converter network, located within the machine but relatively remote from said transducer, for converting said first signal from the electrical charge form to a voltage and current signal characteristic of said vibrations, said converter including an operational amplifier having an output port, an inverting input port, and a non-inverting input port; a first resistor and capacitor pair connected in parallel between the inverting input port and the output port; and a second resistor and capacitor pair connected in parallel between the non-inverting input port and a common connection point; and wherein said first signal is applied between said inverting input port and said non-inverting port to produce said voltage and current signal at said output port substantially free of electrical interference.

2. The apparatus of claim 1 wherein said transducer is a piezoelectric accelerometer.

3. The apparatus of claims 1 or 2 wherein the capacitor of said second resistor and capacitor pair is substantially equal in capacitance to the capacitor of said first resistor and capacitor pair and the resistor of said second resistor nd capacitor pair is substantially equal in resistance to the resistor of said first resistor and capacitor pair.

4. The apparatus of claim 3 wherein the resistors of said first and second resistor and capacitor pairs are each greater than or equal to 200 megohms.

5. Apparatus for producing an analog signal which is substantially free of electrical interference effects and which is characteristic of mechanical vibrations occurring on a component part of an electrical power generator, such apparatus comprising:

a piezoelectric accelerometer affixed to said component part for vibration therewith, said accelerometer being responsive to generate an electrical charge signal indicative of said vibrations;

a charge converter located at some distance from the accelerometer for receiving said charge signal and converting it to an electronic signal indicative of said vibrations, said charge converter including an operational amplifier having a first resistor and capacitor pair connected in parallel between the output and inverting input terminals of said operational amplifier and a second resistor and capacitor pair connected in parallel between the non-inverting input terminal of said operational amplifier and a common reference point, said charge signal being applied directly between the inverting and non-inverting input terminals of said operational amplifier and said electronic signal being produced at the output terminal of said operational amplifier.

6. The apparatus of claim 5 wherein the resistors of said first and second resistor and capacitor pairs are of equal resistance values and the capacitors of said first and second resistor and capacitor pairs are of equal capacitance value.

7. The apparatus of claim 6 wherein the resistors of said first and second resistor and capacitor pairs are greater than or equal to 200 megohms in resistance value.

* * * * *